(12) United States Patent
Collin

(10) Patent No.: US 6,464,967 B1
(45) Date of Patent: Oct. 15, 2002

(54) MAKE-UP COMPOSITION COMPRISING A POLY-ALPHA-OLEFIN

(75) Inventor: Nathalie Collin, Sceaux (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/386,521

(22) Filed: Aug. 31, 1999

(30) Foreign Application Priority Data

Sep. 25, 1998 (FR) ............................................. 98 12043

(51) Int. Cl.⁷ .............................. A61K 7/02; A61K 7/06
(52) U.S. Cl. .................... 424/70.7; 514/937; 424/70.11
(58) Field of Search ........................... 424/70.7, 70.11, 424/70.13, 70.15, 70.16, 70.17, 401; 514/931; 132/218

(56) References Cited

U.S. PATENT DOCUMENTS

| | | | |
|---|---|---|---|
| 3,734,874 A | | 5/1973 | Kibler et al. |
| 3,937,811 A | | 2/1976 | Papantoniou et al. |
| 4,060,569 A | | 11/1977 | Woods et al. |
| 4,233,196 A | | 11/1980 | Sublett |
| 4,239,546 A | | 12/1980 | Russell et al. |
| 4,304,901 A | | 12/1981 | O'Neill et al. |
| 4,534,963 A | * | 8/1985 | Gordon ....................... 424/69 |
| 4,586,520 A | * | 5/1986 | Brittain |
| 5,480,632 A | | 1/1996 | Orr et al. |
| 5,556,613 A | | 9/1996 | Arnaud et al. ................. 424/64 |
| 5,725,845 A | | 3/1998 | Krog et al. |
| 5,750,095 A | | 5/1998 | Arnaud et al. ................. 424/64 |
| 5,925,337 A | * | 7/1999 | Arraudeau et al. ........... 424/63 |

FOREIGN PATENT DOCUMENTS

| | | |
|---|---|---|
| EP | 0 422 862 | 4/1991 |
| EP | 0 547 897 | 6/1993 |
| EP | 0 611 170 | 8/1994 |
| EP | 0 685 221 | 12/1995 |
| EP | 0 792 633 | 9/1997 |
| EP | 0 815 826 | 1/1998 |
| EP | - 819 428 | 1/1998 |
| FR | 2 232 303 | 1/1975 |
| WO | WO 91/12793 | 9/1991 |
| WO | WO 95/15741 | 6/1995 |
| WO | WO 97/35542 | 10/1997 |

OTHER PUBLICATIONS

Merriam–Webster's Collegiate Dictionary, 10 Ed., Merriam–Websters, Inc., Springfield, MA (1998), p. 703.*
Database Derwent on East, week 198245, Derwent Publications Ltd., AN 1982–96016E, Class A61K007/00, JP 57158714 A (Shiseido Co. Ltd.), abstract.*
English Language Derwent Abstract of EP 0 611 170. 1994.
English Language Derwent Abstract of EP 0 685 221. 1995.
English Language Derwent Abstract of EP 0 792 633. 1997.
English Language Derwent Abstract of EP 0 815 826. 1998.
English Language Derwent Abstract of EP 0 819 428. 1998.
English Language Derwent Abstract of FR 2 232 303. 1975.
C.R.C Handbook of Chemistry and Physics 66$^{th}$ Ed. p. F–41, Weast, Ed., CRC Press, Boca Raton, FL, 1986.
English language translation of JP 57–158,174, Sep. 1982.
Hawley's Condensed Chemical Dictionary, p. 819, 1997, 13th Ed, Rehard S. Lewis Sr. Ed., John Wiley & Sons, Inc., New York.
Encyclopedia of Chemical Technology, Kirk–Othmer, vol. 22, 3$^{rd}$Edition, pp. 333–432. 1998.

* cited by examiner

*Primary Examiner*—Russell Travers
*Assistant Examiner*—Alysia Berman
(74) *Attorney, Agent, or Firm*—Finnegan, Henderson, Farabow, Garrett & Dunner, L.L.P.

(57) ABSTRACT

The invention includes a composition for making up keratinous material, in the form of a wax-in-water emulsion, characterized in that it comprises at least one polyolefin wax resulting from the homopolymerization of alpha-olefins having at least 10 carbon atoms, the said wax having a melting point ranging from 50 to 80° C. The composition is preferably intended for making up the lashes.

40 Claims, No Drawings

MAKE-UP COMPOSITION COMPRISING A POLY-ALPHA-OLEFIN

This application claims priority to French application FR 98 12043, filed Sep. 25, 1998.

The present invention relates to a composition for making up keratinous fibres, especially human hair and lashes, which comprises at least one polyolefin wax. The invention additionally relates to the use of this composition for making up keratinous fibres and to a method of making up these fibres. The makeup composition and the makeup method of the invention are intended more particularly for substantially longitudinal keratinous fibres such as the lashes, eyebrows and hair, including false eyelashes and hairpieces. More especially, the invention relates to a mascara.

Mascaras are at present prepared in accordance with two types of formulation: aqueous mascaras, referred to as cream mascaras, which are in the form of an emulsion of waxes in water; and anhydrous mascaras or mascaras with a low water content, referred to as waterproof mascaras, which are in the form of dispersions of waxes in solvents.

It is known to employ various waxes for the formulation of mascaras, such as those described in the document WO-A-91/12793. Depending on their nature, these waxes impart different makeup properties to the mascara. For example, carnauba wax imparts hardness to the film which is deposited on the lashes, whereas beeswax provides good adhesion of the film to the lashes, although in this case the lashes have a tendency to stick together.

In order to obtain optimum makeup properties, it is possible to use mixtures of waxes, as is described in the document WO-A-95/15741. However, the mascaras obtained may not always be easy to apply to the lashes with the current applicators such as mascara brushes: when the mascara is applied to the lashes, contact of the composition with the lash may leave a clinging and dragging sensation. Moreover, when the mascara comprises waxes which are too hard, it may be difficult to work the deposit of product over the lashes using the brush, which can render it difficult either to control making up or to obtain an even coverage of the lashes. Moreover, a rigid film of mascara leaves the user with an uncomfortable sensation and has a tendency to crumble over time, which opposes the production of a makeup featuring a good hold.

The aim of the present invention is to provide a composition for making up keratinous material, and especially fibres such as the lashes, in the form of a wax-in-water emulsion which can go readily onto the keratinous material and which can lead, after application, to a homogeneous makeup which is comfortable to wear and which exhibits a good hold.

The inventors have discovered that a composition of this kind can be obtained by using at least one specific polyolefin wax. A creamy composition can be obtained which can be easy to apply to keratinous material. The made-up keratinous material can be well coated, in a homogeneous fashion. Moreover, the composition can glide well on the lashes and can be easy to work using the brush. The deposit of the makeup product on the lashes therefore can make it possible to modulate the desired makeup with ease on the lashes and, in particular, to control the amount of product to be deposited on the lashes. Furthermore, the polyolefin wax can be highly compatible with the waxes which are presently used in mascaras, which makes it possible to use the polyolefin wax in a mixture with these common waxes without introducing any particular constraint.

The present invention therefore provides a composition for making up keratinous fibres, in the form of a wax-in-water emulsion, characterized in that it comprises at least one polyolefin wax resulting from the homopolymerization of alpha-olefins having at least 10 carbon atoms, the at least one wax having a melting point ranging from 50 to 80° C.

The invention also provides a mascara product comprising a reservoir, which contains a mascara composition, and a brush for applying the above-defined composition to keratinous fibres, especially the lashes.

The invention additionally provides a method of making up keratinous fibres, especially the lashes, which comprises applying a composition as defined above to the keratinous matter.

The invention provides, furthermore, for the use of a composition as defined above to obtain a makeup which is homogeneous and/or easy to apply and/or which has a good hold.

The invention additionally provides for the use of a polyolefin wax as defined above in a composition for making up keratinous fibres in the form of a wax-in-water emulsion.

The polyolefin wax preferably used in the composition of the invention is obtained from the homopolymerization of an alpha-olefin corresponding to the general formula $R$—$CH$=$CH_2$ in which R denotes an alkyl radical having 10 to 50 carbon atoms and preferably 25 to 50 carbon atoms or mixtures thereof. R is preferably a linear alkyl radical. According to the invention, the homopolymerization of an alpha-olefin means the polymerization of monomers consisting essentially of an alpha-olefin or of a mixture of alpha-olefins as defined above.

The polyolefin wax preferably has a needle penetration, measured at 44° C., which ranges from 15 to 120, more preferably from 100 to 120 and, most preferably, from 105 to 115. The polyolefin wax preferably has a melting point ranging from 50° C. to 60° C.

The polyolefin wax can have a number-average molecular weight ranging from 400 to 3000, preferably from 2000 to 3000 and, more preferably, from 2500 to 2700.

Polyolefin waxes of this kind are described in the U.S. Pat. Nos. 4,060,569 and 4,239,546, the disclosures of which are specifically incorporated by reference herein. These waxes are sold in particular under the names "PERFORMA V® 103", "PERFORMA V® 253" and "PERFORMA V® 260" by the company Petrolite.

These waxes have the following characteristics:

|  | PERFORMA V® 103 | PERFORMA V® 253 | PERFORMA V® 260 |
| --- | --- | --- | --- |
| melting point (ASTM Standard D 36) | 74° C. | 67° C. | 54° C. |
| number-average molecular weight | 2800 | 520 | 2600 |
| polydispersity of the molecular weight | 6 | 8 | 11.5 |
| density measured at 25° C. (ASTM Standard D 792) | 0.92 g/cm$^3$ | 0.92 g/cm$^3$ | 0.90 g/cm$^3$ |

-continued

|  | PERFORMA V ® 103 | PERFORMA V ® 253 | PERFORMA V ® 260 |
|---|---|---|---|
| hardness (needle penetration-ASTM standard D 1321) at 25° C. | 5 | 7 | 12 |
| hardness (needle penetration-ASTM standard D 1321) at 44° C. | 20 | — | 110 |
| viscosity at 99° C. (ASTM Standard D 3236) | 0.345 Pa · s (345 centipoises) | 0.006 Pa · s (6 centipoises) | 0.358 Pa · s (358 centipoises) |

The polydispersity of the molecular weight corresponds to the ratio of the weight-average molecular weight to the number-average molecular weight.

The needle penetration of the waxes is determined in accordance with the French standard NF T 60-123 or the American standard ASTM D 1321, at the temperature of 44° C. In accordance with these standards, the needle penetration is the measurement of the depth, expressed in tenths of a millimetre, to which a standard needle, weighing 2.5 g, which is placed in a mobile apparatus weighing 97.5 g and is placed on the wax to be tested, for 5 seconds, penetrates into the wax.

The polyolefin wax preferably has a density ranging from 0.85 to 0.95 g/cm$^3$.

In the composition of the invention the at least polyolefin wax can generally be present in an amount ranging from 0.1% to 20% by weight relative to the total weight of the composition, and preferably from 0.5% to 12% by weight.

The composition of the invention may comprise, in addition to the above-defined polyolefin wax, one or more additional waxes, which can be selected from waxes of animal origin, waxes of plant origin and waxes of synthetic origin.

The additional waxes which can be used in the composition of the invention preferably have a melting point of between 40 and 110° C., inclusive, and a needle penetration ranging from 1 to 217. The needle penetration of the waxes is determined in accordance with the French standard NF T 60-123 or the American standard ASTM D 1321, at the temperature of 25° C. In accordance with these standards, the needle penetration is the measurement of the depth, expressed in tenths of a millimetre, to which a standard needle, weighing 2.5 g, which is placed in a mobile apparatus weighing 97.5 g and is placed on the wax to be tested, for 5 seconds, penetrates into the wax.

Among waxes of animal origin, mention may be made of beeswaxes, lanolin waxes and Chinese insect waxes.

Among waxes of plant origin, mention may be made of rice waxes, carnauba wax, candellila wax and ouricurry wax, cork fibre waxes, sugar cane waxes, Japan waxes, sumach wax and cotton wax.

Among waxes of mineral origin, mention may be made of paraffins, microcrystalline waxes, montan waxes and ozokerites.

Among waxes of synthetic origin, mention may be made in particular of polyethylene waxes, waxes obtained by Fischer-Tropsch synthesis, waxy copolymers and their esters, and silicone waxes.

It is also possible to use hydrogenated oils of animal or plant origin provided that they meet the two abovementioned physical characteristics.

Among these oils, mention may be made of hydrogenated jojoba waxes and hydrogenated oils which are obtained by catalytic hydrogenation of fats composed of a $C_8$–$C_{32}$ linear or nonlinear fatty chain, hydrogenated sunflower oil, hydrogenated castor oil, hydrogenated copra oil, hydrogenated lanolin and hydrogenated palm oils.

The waxes which can be used in accordance with the present invention are preferably solid and rigid at temperatures below 50° C.

The composition of the invention can generally comprise from 0.1% to 30% by weight of additional wax relative to the total weight of the composition, preferably from 1% to 20% by weight.

Preferably, the composition according to the invention can comprise:
at least one additional wax having a needle penetration ranging from 1 to 7.5 (called wax I), in particular in an amount ranging from 0.1% to 20% by weight relative to the total weight of the composition, and
at least one additional wax having a needle penetration of more than 7.5 and less than or equal to 217 (called wax II), in particular in an amount ranging from 0.1% to 10% by weight relative to the total weight of the composition.

According to the invention, the waxes can be present in the composition in the form of particles generally having a size ranging from 50 nm to 10 μm, and preferably from 50 nm to 3.5 μm.

The water content of the composition of the invention can generally range from 20% to 99% by weight, preferably from 50% to 80% by weight, relative to the total weight of the composition.

The composition according to the invention may additionally comprise a film-forming polymer which can be solubilized and/or in the form of particles in dispersion in the aqueous phase.

The film-forming polymer can be selected from:
keratin derivatives, such as keratin hydrolysates and sulphonic keratins;
anionic, cationic, amphoteric or nonionic derivatives of chitin or chitosan;
cellulose derivatives such as hydroxyethylcellulose, hydropropylcellulose, methylcellulose, ethylhydroxyethylcellulose, carboxymethylcellulose, and quaternized derivatives of cellulose;
acrylic polymers or copolymers, such as polyacrylates or polymethacrylates;
polyvinylpyrrolidones and vinyl copolymers, such as methyl vinyl ether-malic anhydride copolymers, or vinyl acetate-crotonic acid copolymer;
water-dispersible anionic polyesteramide and/or polyester polymers, comprising monomers bearing a functional group —SO$_3$M, in which M represents a hydrogen atom, an ammonium ion NH$_4^+$ or a metal ion, such as, for example, an Na$^+$, Li$^+$, K$^+$, Mg$^{2+}$, Ca$^{2+}$, Cu$^{2+}$, Fe$^{2+}$ or Fe$^{3+}$ ion. Mention may be made in particular of the polymers described in the documents U.S. Pat. Nos. 3,734,874; 4,233,196; 4,304,901, the disclosures of which are specifically incorporated by reference herein. Advantageously, the polymers selected will be film-forming polyester polymers based on at least one dicarboxylic acid, at least one diol and at least one bifunctional aromatic monomer which additionally carries a group —$SO_3M$ as described above.

Fatty chain polyesters, polyamides, and epoxy ester resins.

Polyurethane polymers, especially anionic, cationic, nonionic or amphoteric polyurethanes, acrylic polyurethanes, polyvinylpyrrolidone polyurethanes, polyester polyurethanes, polyether polyurethanes, polyureas, polyurea/polyurethanes, and mixtures thereof.

Polymers of natural origin, modified if desired, such as
  gum arabic, guar gum, xanthan derivatives, karaya gum;
  alginates and carragheenates;
  glycoaminoglycans, hyaluronic acid and its derivatives;
  shellac, sandarac gum, dammars, elemis and copals.

The film-forming polymer can be present in the composition in an amount of dry matter generally ranging from 0.1% to 10% by weight relative to the total weight of the composition.

The composition of the invention can comprise emulsifying surfactants which are present in particular in a proportion ranging from 2 to 30% by weight relative to the total weight of the composition, and more preferably from 5% to 15%. These surfactants can be selected from anionic or nonionic surfactants. Reference may be made to the document "Encyclopedia of Chemical Technology, KIRK-OTHMER", volume 22, pp. 333–432, 3rd edition, 1979, Wiley, for the definition of the properties and (emulsifying) functions of the surfactants, in particular pp. 347–377 of this reference, for anionic and nonionic surfactants. The cited pages are specifically incorporated by reference herein.

The surfactants used preferably in the compositions of the invention are:
  among nonionic surfactants: fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$–$C_6$ alkyl glucose fatty esters.
  Among anionic surfactants: $C_{16}$–$C_{30}$ fatty acids neutralized by amines, ammonia or the alkali metal salts.

Preference is given to the use of surfactants which allow an oil-in-water emulsion to be obtained.

Furthermore, the composition may comprise at least one thickener, preferably a hydrophillic thickener. This thickener can be selected, for example, from carboxyvinyl polymers (carbomer), acrylic copolymers such as acrylate-alkyl acrylate copolymers, polyacrylamides, polysaccharides, natural gums, and clays.

The composition of the invention may additionally comprise ingredients which are commonly used in cosmetics, such as vitamins, trace elements, softeners, sequestrants, perfumes, oils, silicones, proteins, ceramides, plasticizers, cohesion agents, and the basifying or acidifying agents which are commonly employed in the cosmetics field, fillers, pigments, emollients and preservatives.

Although not necessarily so, when the composition comprises 1 g of the polyolefin wax "PERFORMA V® 103", the composition preferably does not comprise the following ingredients, in the amounts indicated:
  1.5 g of vinylpyrrolidone/eicosene copolymer,
  2 g of butylene glycol,
  0.35 g of hydroxyethylcellulose,
  4 g of glyceryl stearate,
  4.3 g of beeswax,
  3.1 g of carnauba wax.

The composition of the invention is intended for a mascara product comprising a reservoir which contains the said mascara composition and a system for applying the said composition to keratinous fibres, especially lashes. The reservoir is provided, conventionally, with an opening which accommodates a liquid-removal system. The applicator system comprises a rod equipped at a first end with a brush and at a second end with a cap which is intended for closing the reservoir. A pack of this kind is illustrated in particular in FIG. 7 of the European Patent Application EP-A-611170, which is specifically incorporated herein by reference, in its entirety. It is not considered necessary to the understanding of the present invention to present a drawing.

The person skilled in the art will of course be careful to select the nature and/or amount of this or these additional compounds, if present, such that the advantageous properties of the composition of the invention are not, or not substantially, adversely affected by the envisaged addition.

The composition of the invention can be prepared in accordance with the methods customary in the fields under consideration.

The invention is illustrated in more detail in the following examples.

EXAMPLE 1

A mascara was prepared, having the following composition:

| | |
|---|---|
| Beeswax | 3.6 g |
| Carnauba wax | 2.9 g |
| Pigments | 5.5 g |
| Thickener | 4.6 g |
| Polyolefin wax (PERFORMA V ® 260 from Petrolite) | 11.4 g |
| Stearic acid | 5.8 g |
| Triethanolamine | 2.4 g |
| 2-Amino-2-methyl-1,3-propanediol | 0.5 g |
| D-Panthenol | 0.5 g |
| Preservatives | qs |
| Water | qs to 100 g |

A mascara is obtained which has a creamy consistency and spreads well over the lashes and is easy to work with the brush, which thus makes it possible to obtain a makeup which is homogeneous and provides a perfect coating of the lashes.

EXAMPLE 2

A mascara was prepared, having the following composition:

| | |
|---|---|
| Beeswax | 4.7 g |
| Carnauba wax | 3.7 g |
| Paraffin wax | 12.8 g |
| Polyolefin wax (PERFORMA V ® 260 from Petrolite) | 0.5 g |
| Thickener | 4.6 g |
| Pigments | 7.1 g |
| Stearic acid | 7.1 g |

| | |
|---|---|
| Triethanolamine | 3.7 g |
| D-Panthenol | 0.5 g |
| Mixture of dimethiconol and decamethylpentasiloxane (15/85) (DC2-9071 from Dow Corning) | 5 g |
| Water qs to | 100 g |

The mascara goes onto the lashes easily, with good creaminess, and envelops the lashes perfectly.

What is claimed is:

1. A composition for making up keratinous material, comprising:
    at least one polyolefin wax produced by homopolymerizing at least one alpha-olefin having at least 10 carbon atoms, wherein said at least one polyolefin wax has a melting point ranging from 50 to 80° C. and further wherein said composition is in the form of a wax-in-water emulsion.

2. The composition according to claim 1, wherein said keratinous material is hair or lashes.

3. The composition according to claim 2, wherein said keratinous material is human hair or lashes.

4. The composition according to claim 1, wherein said at least one polyolefin wax has a melting point ranging from 50° C. to 60° C.

5. The composition according to claim 1, wherein said at least one polyolefin wax has a needle penetration ranging from 15 to 120 when measured at 44° C. using the ASTM D 1321 or NF T 60-123 standard.

6. The composition according to claim 5, wherein said at least one polyolefin wax has a needle penetration ranging from 100 to 120 when measured at 44° C. using the ASTM D 1321 or NF T 60-123 standard.

7. The composition according to claim 6, wherein said at least one polyolefin wax has a needle penetration ranging from 105 to 115 when measured at 44° C. using the ASTM D 1321 or NF T 60-123 standard.

8. The composition according to claim 1, wherein said at least one polyolefin wax has a number-average molecular weight ranging from 400 to 3000.

9. The composition according to claim 1, wherein said at least one polyolefin wax has a number-average molecular weight ranging from 2000 to 3000.

10. The composition according to claim 9, wherein said at least one polyolefin wax has a number-average molecular weight ranging from 2500 to 2700.

11. The composition according to claim 1, wherein said at least one polyolefin wax has a density ranging from 0.85 to 0.95 g/cm$^3$ when measured at 25° C. using the ASTM Standard D 792.

12. The composition according to claim 1, wherein said at least one polyolefin wax is produced by homopolymerizing at least one alpha-olefin of formula R—CH=CH$_2$, in which R is chosen from alkyl radicals having from 10 to 50 carbon atoms.

13. The composition according to claim 12, wherein R is chosen from alkyl radicals having from 25 to 50 carbon atoms.

14. The composition according to claim 12, wherein said alkyl radicals are linear.

15. The composition according to claim 13, wherein said alkyl radicals are linear.

16. The composition according to claim 1, wherein said at least one polyolefin wax is present in an amount ranging from 0.1% to 20% by weight relative to the total weight of said composition.

17. The composition according to claim 1, wherein said at least one polyolefin wax is present in an amount ranging from 0.5% to 12% by weight relative to the total weight of said composition.

18. The composition according to claim 1, further comprising at least one additional wax having an origin chosen from animals, plants and synthetic origins.

19. The composition according to claim 18, wherein said at least one additional wax has a needle penetration ranging from 1 to 217 when measured at 25° C. using the ASTM D 1321 or NF T 60-123 standard.

20. The composition according to claim 18, wherein said composition comprises at least two additional waxes,
    wherein at least one additional wax has a needle penetration ranging from 1 to 7.5 when measured at 25° C. using the ASTM D 1321 or NF T 60-123 standard, wherein said other at least one additional wax has a needle penetration greater than 7.5 and less than or equal to 217 when measured at 25° C. using the ASTM D 1321 or NF T 60-123 standard.

21. The composition according to claim 20, wherein said at least two additional waxes are present in an amount ranging from 0.1% to 30% by weight relative to the total weight of said composition.

22. The composition according to claim 21, wherein said at least two additional waxes are present in an amount ranging from 1% to 20% by weight relative to the total weight of said composition.

23. The composition according to claim 18, wherein said at least one additional wax is present in an amount ranging from 0.1% to 30% by weight relative to the total weight of said composition.

24. The composition according to claim 23, wherein said at least one additional wax is present in an amount ranging from 1% to 20% by weight relative to the total weight of said composition.

25. The composition according to claim 19, wherein said at least one additional wax is present in an amount ranging from 0.1% to 30% by weight relative to the total weight of said composition.

26. The composition according to claim 25, wherein said at least one additional wax is present in an amount ranging from 1% to 20% by weight relative to the total weight of said composition.

27. The composition according to claim 1, further comprising at least one film-forming polymer.

28. The composition according to claim 27, wherein said at least one film-forming polymer is solubilized or is in the form of dispersed particles in the aqueous phase of said composition.

29. The composition according to claim 27, wherein the dry matter of said at least one film-forming polymer is present in an amount ranging from 0.1% to 10% by weight relative to the total weight of said composition.

30. The composition according to claims 28, wherein the dry matter of said at least one film-forming polymer is present in an amount ranging from 0.1% to 10% by weight relative to the total weight of said composition.

31. The composition according to claim 1, further comprising at least one emulsifying surfactant.

32. The composition according to claim 31, wherein said at least one emulsifying surfactant is present in an amount ranging from 2% to 30% by weight relative to the total weight of said composition.

33. The composition according to claim 1, further comprising at least one thickener.

34. The composition according to claim 1, further comprising at least one additive chosen from: vitamins, trace elements, softeners, sequestrants, perfumes, oils, silicones, vitamins, proteins, ceramides, plasticizers, cohesion agents, basifying agents, acidifying agents, fillers, pigments, emollients and preservatives.

35. The composition according to claim 1, wherein water is present in an amount ranging from 20% to 99% by weight relative to the total weight of said composition.

36. The composition according to claim 35, wherein water is present in an amount ranging from 50% to 80% by weight relative to the total weight of said composition.

37. A mascara product, comprising:
  a reservoir which contains a mascara composition and a brush for applying said composition to keratinous fibres;
  wherein said mascara composition comprises: a composition which comprises:
  at least one polyolefin wax produced by homopolymerizing at least one alpha-olefin having at least 10 carbon atoms, wherein said at least one polyolefin wax has a melting point ranging from 50 to 80° C. and further wherein said composition is in the form of a wax-in-water emulsion.

38. A method of making up keratinous material, comprising applying to said keratinous material an effective amount of a composition which comprises:
  at least one polyolefin wax produced by homopolymerizing at least one alpha-olefin having at least 10 carbon atoms, wherein said at least one polyolefin wax has a melting point ranging from 50 to 80° C. and further wherein said composition is in the form of a wax-in-water emulsion.

39. The method according to claim 38, wherein said keratinous material is a human lash and said composition is a mascara composition.

40. A mascara, comprising a composition which comprises:
  at least one polyolefin wax produced by homopolymerizing at least one alpha-olefin having at least 10 carbon atoms, wherein said at least one polyolefin wax has a melting point ranging from 50 to 80° C. and further wherein said composition is in the form of a wax-in-water emulsion.

* * * * *